(12) United States Patent
Rios et al.

(10) Patent No.: US 10,479,972 B2
(45) Date of Patent: Nov. 19, 2019

(54) CHAMBER FOR IMAGING CELLS AND METHOD OF USE THEREOF

(71) Applicants: RUSH UNIVERSITY MEDICAL CENTER, Chicago, IL (US); LOYOLA UNIVERSITY CHICAGO, Maywood, IL (US)

(72) Inventors: Eduardo Rios, Chicago, IL (US); Peter Caron, Villa Park, IL (US); Pieter deTombe, Oak Park, IL (US); Carlo Manno, Chicago, IL (US)

(73) Assignees: RUSH UNIVERSITY MEDICAL CENTER, Chicago, IL (US); LOYOLA UNIVERSITY CHICAGO, Maywood, IL (US)

( * ) Notice: Subject to any disclaimer, the term of this patent is extended or adjusted under 35 U.S.C. 154(b) by 233 days.

(21) Appl. No.: 15/567,132

(22) PCT Filed: Apr. 6, 2016

(86) PCT No.: PCT/US2016/026097
§ 371 (c)(1),
(2) Date: Oct. 17, 2017

(87) PCT Pub. No.: WO2016/171902
PCT Pub. Date: Oct. 27, 2016

(65) Prior Publication Data
US 2018/0087016 A1 Mar. 29, 2018

Related U.S. Application Data

(60) Provisional application No. 62/149,976, filed on Apr. 20, 2015.

(51) Int. Cl.
*C12M 1/22* (2006.01)
*C12M 1/00* (2006.01)
(Continued)

(52) U.S. Cl.
CPC ............ *C12M 23/10* (2013.01); *C12M 29/10* (2013.01); *C12M 35/02* (2013.01); *C12M 41/36* (2013.01); *G02B 21/0004* (2013.01); *G02B 21/34* (2013.01)

(58) Field of Classification Search
CPC ...... C12M 23/10; C12M 29/10; C12M 35/02; C12M 41/36; G02B 21/0004; G02B 21/34
See application file for complete search history.

(56) References Cited

U.S. PATENT DOCUMENTS 3,726,597 A     4/1973   Dvorak et al.
6,117,291 A *   9/2000   Olesen ............. G01N 33/48728
                                                     204/415

(Continued)

OTHER PUBLICATIONS

International Search Report and Written Opinion for PCT/US2016/026097 dated Jul. 12, 2016, 10 pgs.

*Primary Examiner* — Michael L Hobbs
(74) *Attorney, Agent, or Firm* — Brinks Gilson & Lione

(57) ABSTRACT

One aspect of the invention provides a sample chamber for use in the dynamic imaging of cells. In one embodiment, the chamber includes a holding mechanism for positioning the cells against a viewing window in the chamber. A housing is positioned against the viewing window to define the closed chamber. The housing may include access ports allowing for the perfusion of fluid through the chamber, the control of the internal temperature of the chamber and the micromanipulation and electrical stimulation of the cells.

17 Claims, 11 Drawing Sheets

(51) Int. Cl.
*C12M 1/42* (2006.01)
*C12M 1/34* (2006.01)
*G02B 21/34* (2006.01)
*G02B 21/00* (2006.01)

(56) References Cited

U.S. PATENT DOCUMENTS

| | | |
|---|---|---|
| 6,461,860 B2 | 10/2002 | Mathes et al. |
| 6,670,170 B1 | 12/2003 | Gaffin et al. |
| 7,718,423 B2 * | 5/2010 | Tsuchiya ............ G01N 21/0332 |
| | | 219/201 |
| 8,294,757 B2 | 10/2012 | Yu et al. |
| 2011/0250690 A1 * | 10/2011 | Craig ....................... A01N 1/02 |
| | | 435/404 |

* cited by examiner

SECTION A-A
SCALE 6

DETAIL B
SCALE 10
View of wire tight against the coverslip

CHAMBER FOR IMAGING CELLS AND METHOD OF USE THEREOF

RELATED APPLICATIONS

This application is a National Stage of PCT/US2016/026097, filed Apr. 6, 2016, which claims the benefit of the filing date of U.S. Provisional Patent Application No. 62/149,976, filed Apr. 20, 2015, the contents of which applications are hereby incorporated by reference.

STATEMENT AS TO RIGHTS TO INVENTIONS MADE UNDER FEDERALLY SPONSORED RESEARCH AND DEVELOPMENT

This invention was made with Government support of Grant No. GM111254 awarded by the National Institutes of Health. The Federal Government has certain rights in this invention.

TECHNICAL FIELD

The present invention generally relates to a chamber for use in the dynamic imaging of cells. In one embodiment, the chamber base assembly includes a cell-holding bay having a holding mechanism for positioning the cells against a viewing window in a wall of the chamber base. A housing is positioned against the chamber base assembly and encloses the cell-holding bay. The housing may include access ports allowing for the perfusion of fluid through the cell-holding bay, the control of the internal temperature of the chamber and the micromanipulation and electrical stimulation of the cells.

BACKGROUND

The standard techniques of cell physiology and biophysics sometimes require immobilizing a cell or a group of cells in a transparent chamber, for microscopic observation while the cell or cells are being manipulated in ways conducive to displaying their functional roles. In most cases this observation is performed on the stage of a microscope. To maximize the optical resolution of the images, microscope objectives of high numerical aperture are used. These require accurate and close positioning of cells flush with a transparent wall of the chamber. Other requisites for such a chamber include the ability for fast exchange of solutions, ability to rapidly temperature variation and control, and free access from the top to micro-manipulated tools, pipettes, electrodes or fiber optic conduits. The cells must be firmly held, as physical movement is detrimental to imaging. At the same time the holding procedure should conserve cellular integrity and functionality, which in this case includes electrical and contractile properties. Chamber materials must be inert, and resist breakage and decay when subject to mechanical and chemical stress. Ease of replacement of components of the chamber is also required.

Some aspects of the design of such a device are particularly applicable to the imaging or muscle cells or fibers and therefore they may be of interest to the several hundred laboratories that conduct experiments with such cells. However, such a chamber will find application in work with other tissues, for example nerve cells or fibers, small vessels, pieces of hollow organ walls and multicellular epithelial preparations.

SUMMARY OF THE PREFERRED EMBODIMENTS

One aspect of the present invention provides an apparatus for imaging cells. In one embodiment, the apparatus includes a chamber base assembly having a cell-holding bay. At least a portion of the floor of the bay is transparent to allow for viewing of the cells in the bay. The cell or bundle of cells is held flush to the viewing window by two cell-holding assemblies. A first cell-holding assembly extends through a first conduit in the chamber base assembly and includes an internal end that may be positioned at a first position in the cell-holding bay. A second cell-holding assembly extends through a second conduit in the chamber base assembly and includes an internal end that may be positioned at a second position in the cell-holding bay.

A chamber perfusion and manipulations manifold ("PMM") is mounted on the chamber base assembly above the cell-holding bay. The internal ends of the first and second cell-holding assemblies are movable between a first position holding the cells against the viewing window and a second position away from the viewing window and allowing initial placement as well as removal of the cells from the cell-holding bay.

In one embodiment, the first cell-holding assembly includes a cell-holding wire forming the internal end of the assembly, a cylindrical rotatable linkage member having an internal end connecting to the cell-holding wire and extending through the first conduit to the exterior of the chamber base assembly, and a handle joined by a flexible connector to the external end of the linkage member.

The cell-holding wire may be a step-shaped wire comprising a first end portion, second end portion and a central portion joining the first end portion to the second end portion. In one such embodiment, the first end portion extends substantially perpendicularly from an eccentric hole in the internal end of the cylindrical member such that rotation of the cylindrical member allows for positioning of the second end portion of the cell-holding wire to hold the cells against the viewing window or positioning of the second end portion of the cell-holding wire away from the viewing window.

In various embodiments, the apparatus also includes at least one fluid entry line that is held by the PMM, and reaches a fluid entry port at the upstream end of the cell-holding bay. The PMM may also hold a fluid exit line extending from a fluid exit port at the downstream end of the cell-holding bay, through the PMM to a fluid aspiration device exterior to the chamber. Both entry and exit ports may be funnel-shaped and of depth gradually increasing towards the cell-holding bay, features designed to minimize turbulence of fluid flow. The apparatus may also include a temperature control unit positioned in the chamber base and providing for temperature control of the cell-holding bay.

In another embodiment, the apparatus may include a first and a second electrical connector positioned on the base of the cell-holding bay and in electrical contact with electrical terminals exterior to the chamber. Such connectors may allow for electrical stimulation of the cell or cells positioned in the cell-holding bay.

In one embodiment, the chamber base assembly and the PMM are manufactured using 3D printing. This method allows for details of shape that are not available with traditional machining or molding methods, as well as changes of the shape in successive versions used, for example, to optimize laminar flow of perfusion fluid and minimization of solution exchange times.

Another aspect of the present invention provides a microscope system for imaging cells. In one embodiment, the microscope system includes an optical microscope unit and an apparatus as disclosed herein. The apparatus may be placed adjacent to the objective lens, in a conventional inverted microscope configuration, such that the cells or fibers contained in the cell-holding bay may be microscopically imaged through the viewing window. For fluorescence or transmitted-light imaging the cells or fibers are illuminated through the microscope objective and the viewing window. For direct viewing, illumination may be provided from above, entering through a separate window in the PMM component.

DETAILED DESCRIPTION OF THE PREFERRED EMBODIMENTS

Definitions

Figure 1:
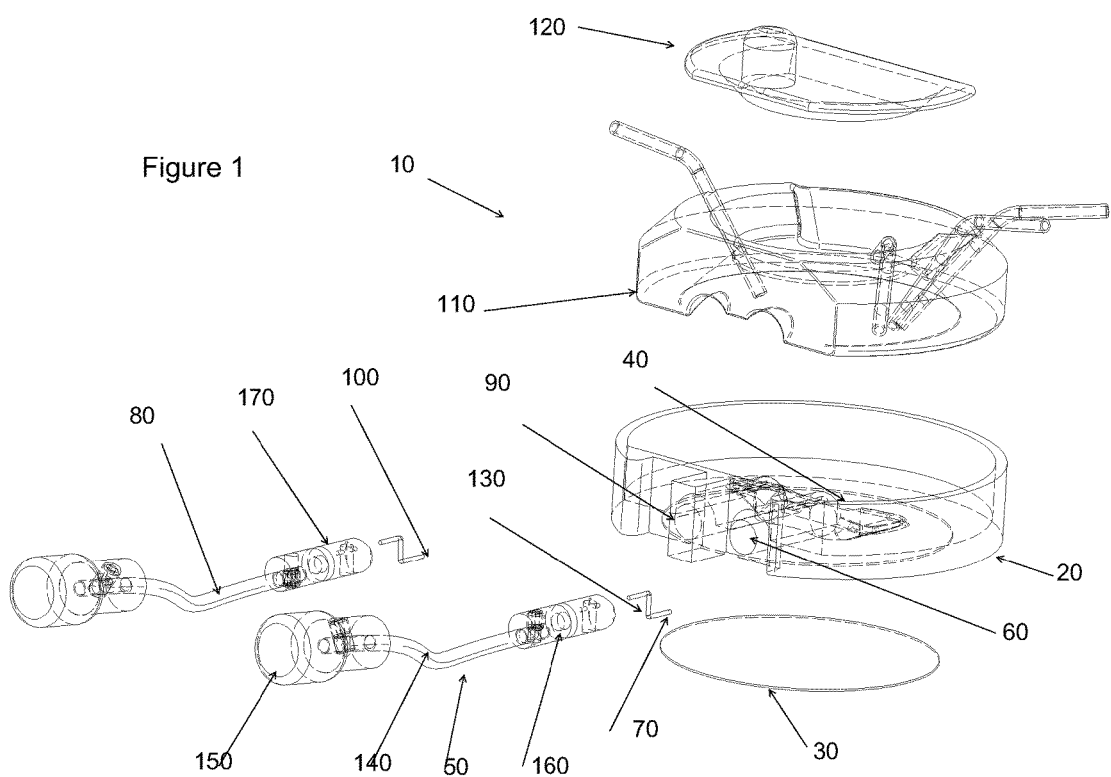
FIG. 1 is an illustration showing an exploded view of one embodiment of an apparatus of the present embodiments.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

Apparatus for Imaging Cells

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. In the discussions that follow, a number of potential features or selections of apparatus and systems, methods of analysis, or other aspects, are disclosed. It is to be understood that each such disclosed feature or features can be combined with the generalized features discussed, to form a disclosed embodiment of the present invention.

Turning now to FIG. 1. This figure illustrates an exploded view of one embodiment of an apparatus of the present invention. The apparatus 10 includes chamber base assembly 20 having viewing window 30, which forms the base of cell-holding bay 40. A first cell-holding assembly 50 extends through first conduit 60 in chamber base assembly 20 and includes first end 70 positionable at a first position in cell-holding bay 40. Second cell-holding assembly 80 extends through second conduit 90 in the chamber base assembly 20 and includes first end 100 positionable at a second position in sample holding bay 40.

Chamber perfusion and manipulations manifold ("PMM") 110 is mounted on the chamber base assembly 20 above cell-holding bay 40. In one embodiment, PMM 110 is held firmly attached to chamber base assembly 20 by magnets positioned in one or both of these components. In another embodiment, detachable lid 120 forms the top of PMM 110. However, in other embodiments, the top of PMM 110 is not detachable. In certain embodiments, the top of PMM 110 or detachable lid 120 may include a transparent window to, for example, allow for illumination of the cells of fibers positioned in cell-holding bay 40. The internal ends of the first cell-holding assembly 50 and second cell-holding assembly 80 are movable between a first position holding the cells against the top side of viewing window 30 and a second position away from the viewing window and allowing for initial placement and removal of the cells or fibers from cell-holding bay 30 after their observation.

In the embodiment illustrated in FIG. 1, first cell-holding assembly 50 includes cell-holding wire 130 forming the internal end of first cell-holding assembly 50. Linkage member 140 includes an internal end connecting to cell-holding wire 130 and in operation is positioned to extend through first conduit 60 to an exterior end, which connects to handle 150 at the exterior of chamber base assembly. In one embodiment, linkage member 140 includes a flexible member having an exterior end attached to handle 150 and a cylindrical member 160 positioned within first conduit 60 and having an exterior end attached to the internal end of the flexible member and an internal end attached to cell-holding wire 130.

Turning now to FIG. 2. FIG. 2(A) shows a plan view of chamber 10 with first cell-holding assembly 50 and second cell-holding assembly 80 positioned within conduits 60 and 90 respectively. FIG. 2(B) is a cross section view along axis A-A illustrating second cell-holding assembly 80 within conduit 90. FIG. 2(C) is an enlarged view of the cell-holding bay 40 showing second cell-holding assembly 80 extending through second conduit 90 in chamber base assembly 20. Internal end 100 of second cell-holding assembly 80 is positioned against viewing window 30 of sample holding bay 40. FIG. 2(D) is a cross section view along axis C-C illustrating the relative positions of cylindrical member 160 of first cell-holding assembly 50 and cylindrical member 170 of second cell-holding assembly 80 within sample holding bay 40. FIG. 2(D) is an enlarged view of this region, illustrating the positioning of internal end 70 of first cell-holding assembly 50 and the internal end 100 of second cell-holding assembly 80 against the top of viewing window 30.

Figure 3:
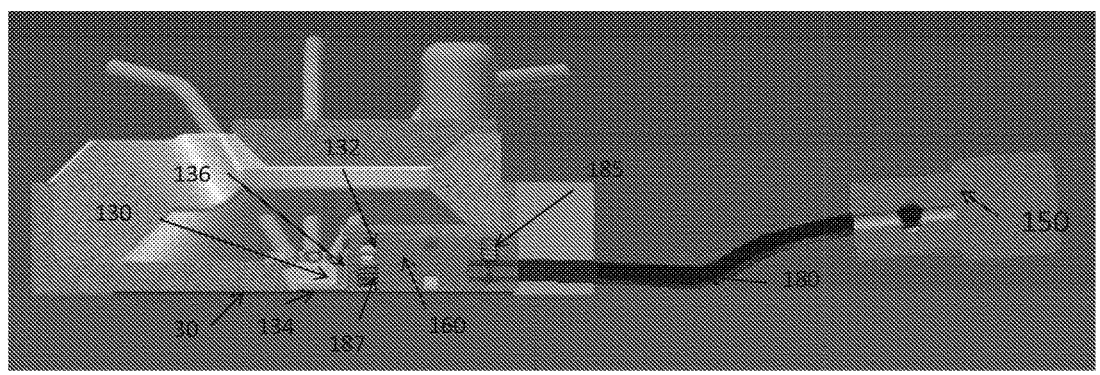
FIG. 3 is a cross section view of one embodiment of the apparatus of the present embodiments.

Turning now to FIG. 3. This figure is an enlarged cross section view of the apparatus illustrating the relative positions of cell-holding wire 130, cylindrical member 160 of first cell-holding assembly 50, and flexible member 180 of linkage member 140. Cell-holding wire 130 is a step-shaped wire comprising a first end portion 132, second end portion 134 and a central portion 136 joining first end portion 132 to the second end portion 134. First end portion 132 of the cell-holding wire 130 extends substantially perpendicularly from an eccentric (off-center) hole in the internal end of the cylindrical member 160 such that rotation of cylindrical member 160 allows for positioning of second end portion 134 of cell-holding wire 130 to hold cells against viewing window 30 or positioning of second end portion 134 of cell-holding wire 130 away from the viewing window 30. In one embodiment, flexible member 180 of linkage member 140 is held to cylindrical member 160 by positioning screw 185, while first end portion 132 of cell-holding wire 130 is held to cylindrical member 160 by positioning screw 187.

Rotation of handle 150 results in the rotation of cylindrical member 160 such that second end portion 134 of cell-holding wire 130 is moved towards or away from the top of viewing window 30, depending on the direction of rotation. At least a part of second end portion 134 extends substantially parallel to the top of viewing window 30. Center portion 136 of cell-holding wire 130 is of a length such that rotation of cylindrical member 160 brings at least a portion of second end portion 134 close enough to the top of viewing window 30 to hold the cell or cells against the viewing window.

In the embodiment illustrated in FIGS. 1 and 3, first end portion 132 and second end portion 134 of cell-holding wire 130 are shown as being parallel to each other, while center portion 136 is shown as being perpendicular to both end portions. However, the present invention also encompasses other embodiments of such a step-shaped cell-holding wire, including those embodiments in which the end portions deviate from parallel and/or where the center portion intersects the first and second end portions at an angle other than perpendicular. In addition, all three portions may include bends or other discontinuities. In one embodiment of the invention, second cell-holding assembly 80 has the same configuration as described above with respect to first cell-holding assembly 50.

In one preferred embodiment, the cylindrical members are almost flush with the top of the viewing window. The holding wires are secured to the cylinder members and shaped so that the portion that comes in contact with the cells slightly exceeds the radius of the cylinder member. Such a configuration allows the holding wires to apply pressure to hold the cells or fibers to the viewing window when rotated, firmly securing the cells or fibers in place.

In one embodiment, the first and second cell-holding wires may be rotated so as to exert a stretching force on cells or fibers positioned in the cell-holding bay. For example, the handles may be moved, one in a clockwise direction, the other in an anti-clockwise direction, so that the holding wires approach the cells or fibers from their central portion and, by pulling in opposite directions, stretch the central portion of the cells or fibers upon contact. Applying such a stretching force may assist in positioning and preventing movement of the cell or fiber, while ensuring that it is placed as close as possible to the window. This close placement is often required given the small working distance of the high numerical aperture objectives used in high resolution imaging.

In various embodiments, the apparatus of the present invention also includes at least one and preferably multiple fluid entry lines extending from the exterior of the PMM, through the PMM, to a fluid entry line end positioned to deliver fluid into the cell-holding bay. In one embodiment, this delivery is into an input port, shown, for example, in FIG. 5, formed at the first (upstream) end of the cell-holding bay. The apparatus may also include at least one fluid exit line extending from a fluid exit port at the second (downstream) end of the cell-holding bay, through the PMM to a fluid aspiration port position exterior to the chamber. In such embodiments, fluids may be delivered to and aspirated from the vicinity of cells or fibers positioned in the cell-holding bay in a continuous perfusion regimen. Both fluid entry and exit regions may be funnel-shaped and of a depth gradually increasing towards the cell-holding bay, features designed to minimize turbulence of solution flow.

Figure 4:
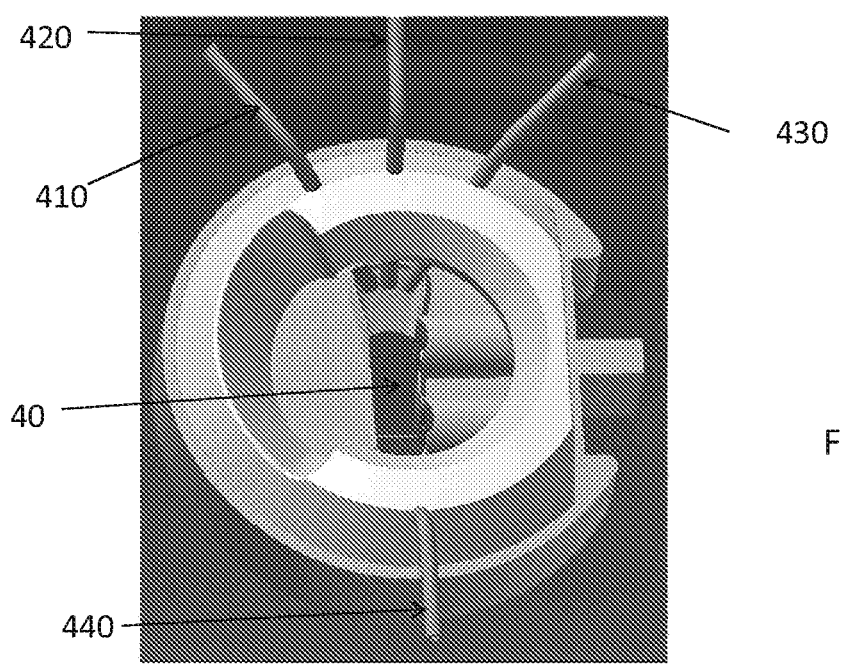
FIG. 4 is an illustration showing a plan view of one embodiment of an apparatus of the present invention.

FIG. 4 shows a plan view of one such embodiment. Here, fluid entry lines 410, 420 and 430 allow for the delivery of fluids to cell-holding bay 40 while fluid exit line 440 provides a means of removing fluids from the cell-holding bay. In certain embodiments, a continuous flow of fluid may be provided through the cell-holding bay to bath the cells or fibers position within. For example, the chamber is designed to allow for rapid flow and exchange of perfusing solutions. In various embodiments, the apparatus includes 1, 2, 3, 4, 5, 6 or more fluid entry lines, allowing for rapid simultaneous or sequential delivery of multiple fluids to the cell-holding bay. Delivery of pre-heated or pre-cooled fluids is possible, as one of multiple ways to control and rapidly change the temperature of the cells.

Figure 5:
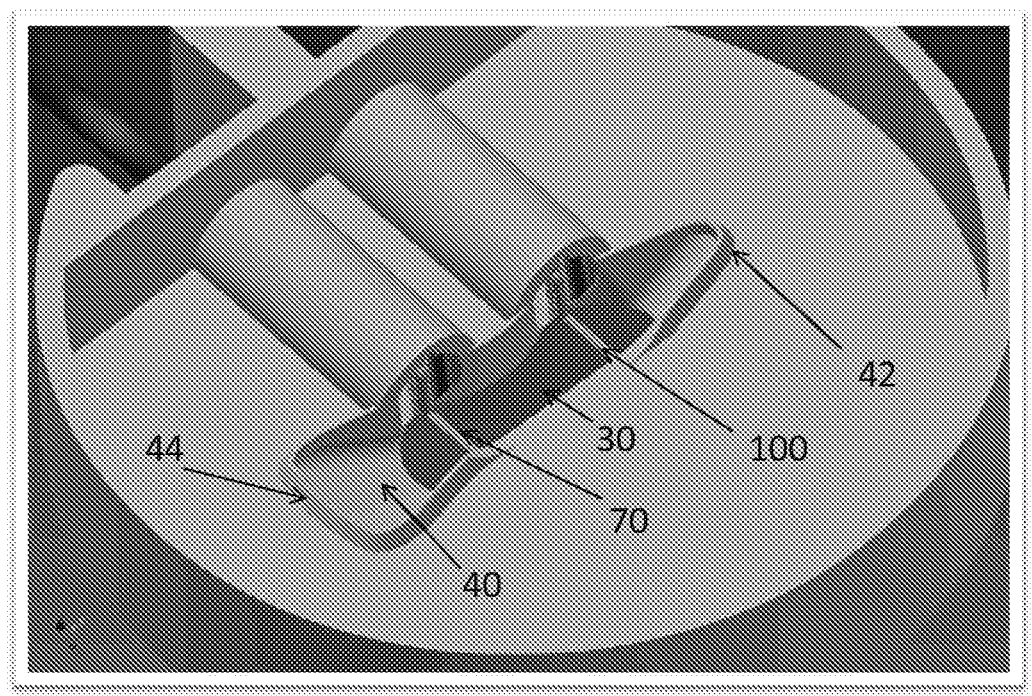
FIG. 5 illustrates one embodiment of a cell-holding bay. The ends of cell-holding assemblies are illustrated positioned to hold cells against the viewing window.
Figure 6:
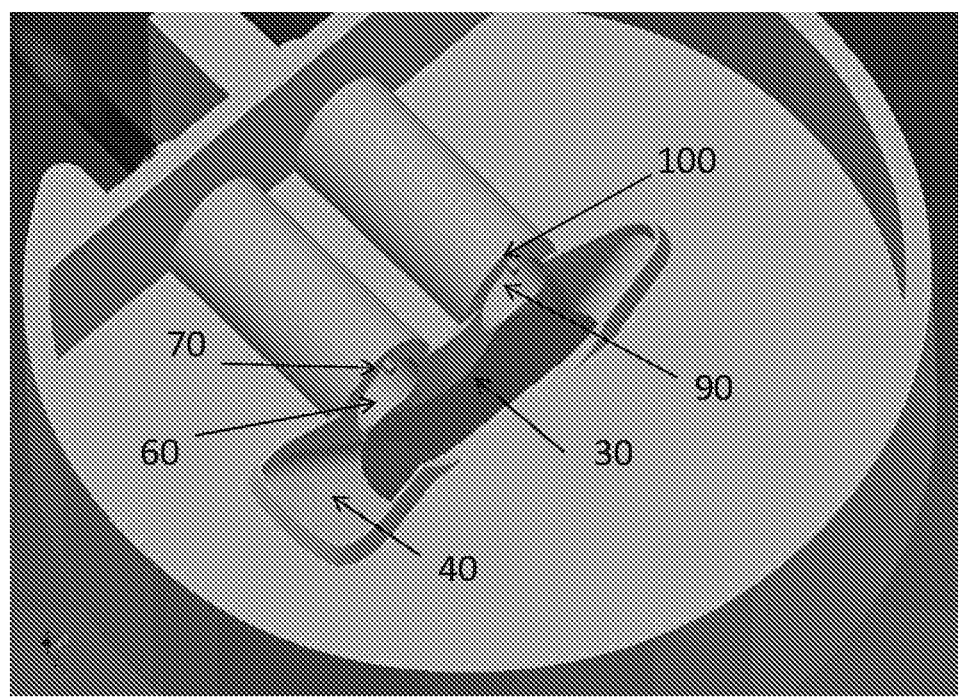
FIG. 6 illustrates one embodiment of a cell-holding bay. The ends of cell-holding assemblies are illustrated positioned within conduits in the chamber base assembly.
Figure 7:
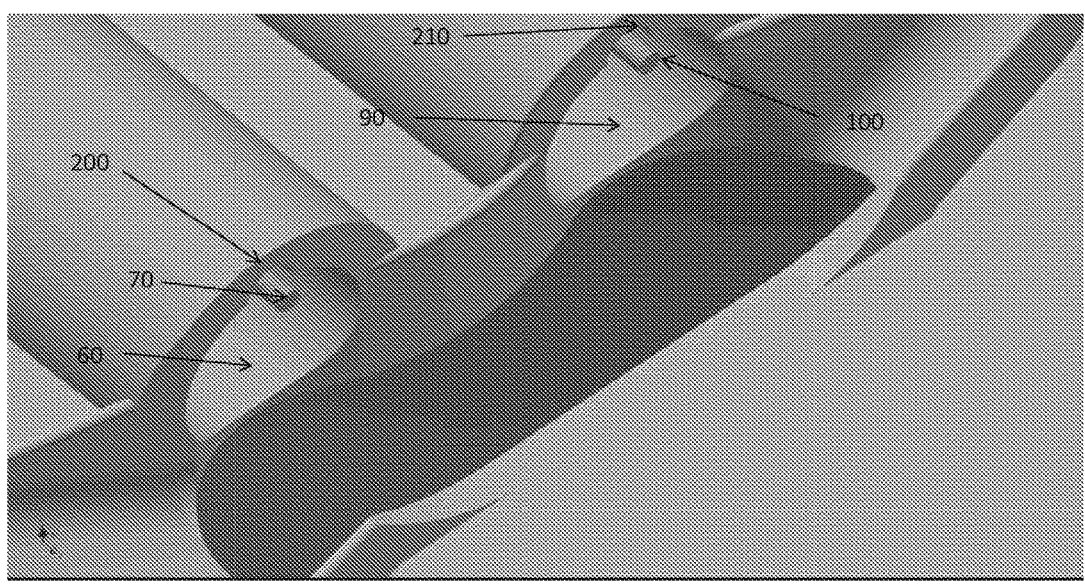
FIG. 7 is a partial enlarged view of FIG. 6 illustrating the positioning of the ends of the cell-holding wires within grooves in the walls of the conduits.

FIG. 5 illustrates one embodiment of a chamber base assembly including a cell-holding bay 40. In this embodiment, the cell-holding bay is formed as a depressed portion of the chamber base assembly. Viewing window 30 forms the base of the cell-holding bay. Input (left) and exit (right) ports are shaped to minimize turbulence and maximize speed of solution change. The cell-holding bay may also include raised lip portions 42 and 44 providing for additional containment of fluid, particularly in cases of rapid fluid flow. In this figure, cell-holding wire end portions 70 and 100 are shown in their cell-holding positions, i.e. positioned against the top of viewing window 30. FIG. 6 also illustrates the chamber base assembly. However, here the cell-holding wire end portions 70 and 100 are shown retracted into conduits 60 and 90 respectively. Thus, in certain embodiments, the holding wires may not only be rotated away from the top of the viewing window by rotating the handles of the cell-holding assemblies but may also be retracted into the conduits by pulling the handles away from the chamber. In this position the screw 187 (FIG. 3) becomes accessible from the outside of the chamber base, for disassembly of cell-holding device. In this position the wire end portions 70 and 100 may be lodged in clearance grooves in the wall of the conduits 60 and 90. Such a positioning is illustrated in FIG. 7. Here, wire end portions 70 and 100 are positioned within grooves 200 and 210 respectively. These grooves should not extend to the external surface of the chamber base, as this may allow fluid to leak from the cell-holding bay.

In certain embodiments, the top of the cell-holding bay is open and continuous with the interior lumen of the PMM. In other embodiments the chamber top is closed, except for its fluid inlet(s) and outlet(s). Closing the top of the chamber reduces the volume of the bay and allows for faster hydrodynamically smooth (laminar) fluid flow through the chamber, enabling a full fluid exchange in a brief time interval. Fast solution exchange can offer advantages for drug testing and other interventions.

For example, a full fluid exchange may be achieved in less than 0.2 sec. In some embodiments, the volume of the cell-holding bay (perfusion compartment) is less than 50, 40, 36, 30 or 25 microliters. In those embodiments in which the cell-holding bay in closed as described above, the PMM may be solid or hollow with a base shaped to fit over the top of the cell-holding bay and close the top of the bay. In certain embodiments, a solid PMM is formed of a transparent or translucent material or has a window formed from such a material. Such a construction allows for viewing of the cell-holding bay through the PMM.

The apparatus may include additional features allowing manipulation of the cells or fibers positioned in the cell-holding bay. In one embodiment, a temperature control unit, for example a Peltier device, is positioned in the chamber, for example in the chamber base assembly or a part of the chamber PMM and provides for temperature control of the cell-holding bay. In other embodiments, the entire apparatus may be combined with a separate heating/cooling stage, such as those supplied by Physitemp Instruments, Inc., Clifton, N.J. 07013. In certain such embodiments, the two large indentations in the chamber base (shown at the right hand side of FIG. 4 and at top left corner of FIGS. 5 and 6) may provide clearance for flexible wires 180 when the full assembly is placed within a cylindrical heating/cooling stage.

In yet other embodiments, the apparatus provides for electrical stimulation of cells within the cell-holding bay. For example, electrical connectors may be positioned on the base of the cell-holding bay, or simply connected outside the chamber base to the cell-holding assemblies to allow for an electrical stimulus to be applied to the cells or fibers positioned in the bay. In one embodiment the electrical connectors inside the cell-holding bay are the cell-holding assemblies themselves, which therefore operate as electrodes in their intra-chamber portions, as well as connectors to the terminals exterior to the chamber. In one embodiment, electrodes may provide for the imposition of an electric field within the cell-holding bay. The electric field may be a spatially homogeneous electric field.

Figure 2A:
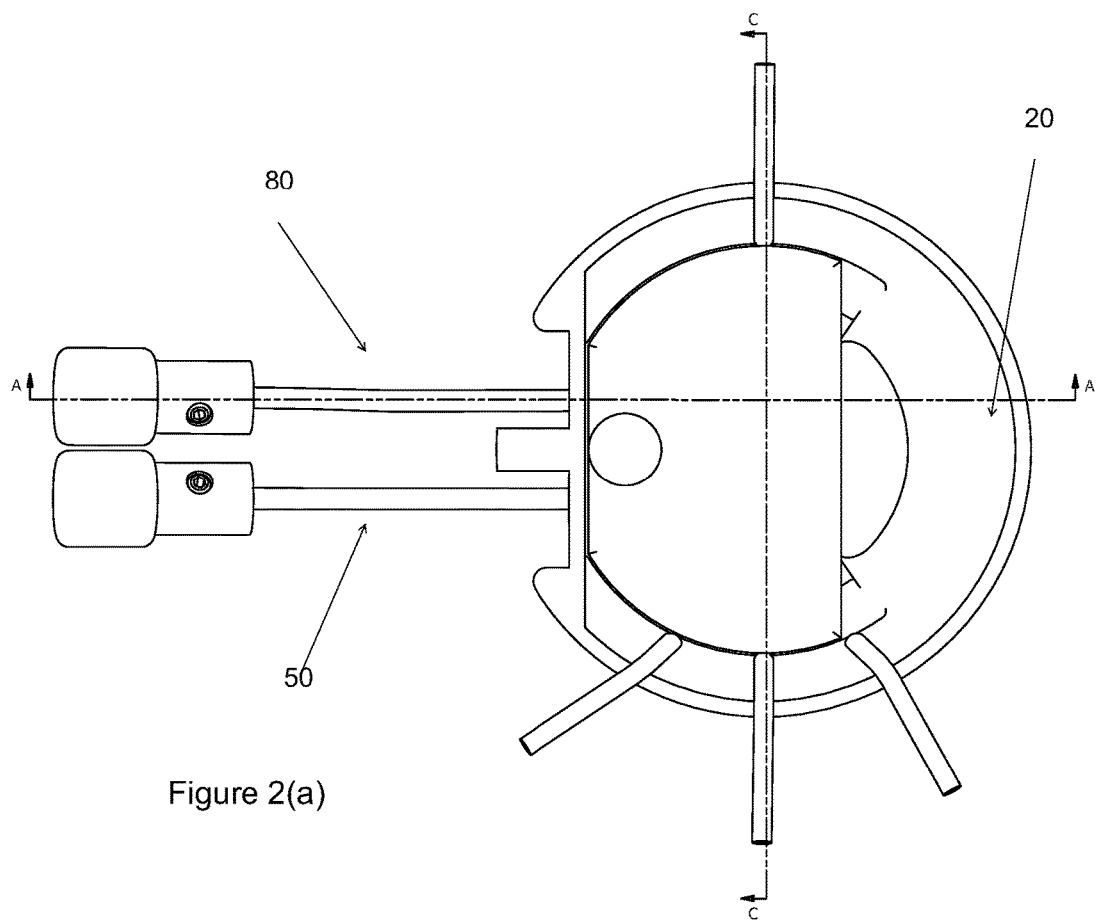
FIGS. 2 (A-E) are illustrations showing elevation, cross section plan and cross section side views of the embodiment of FIG. 1, along with detailed views of this embodiment.
Figure 2B:
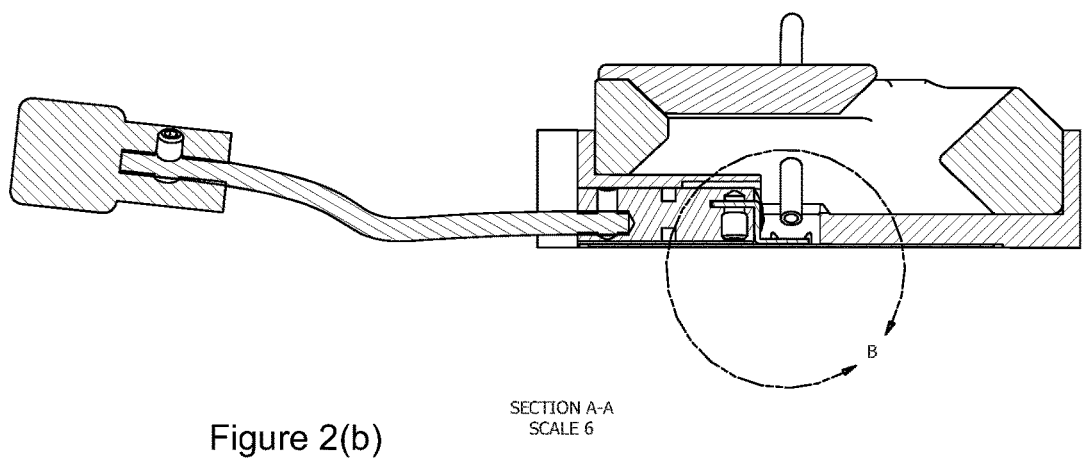
Figure 2C:
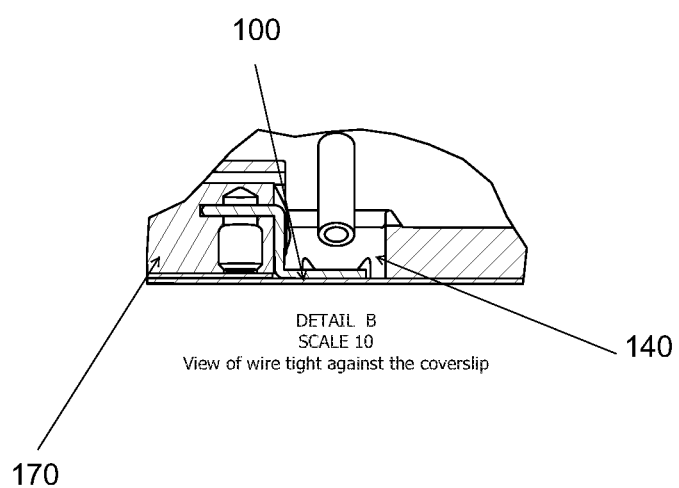
Figure 2D:
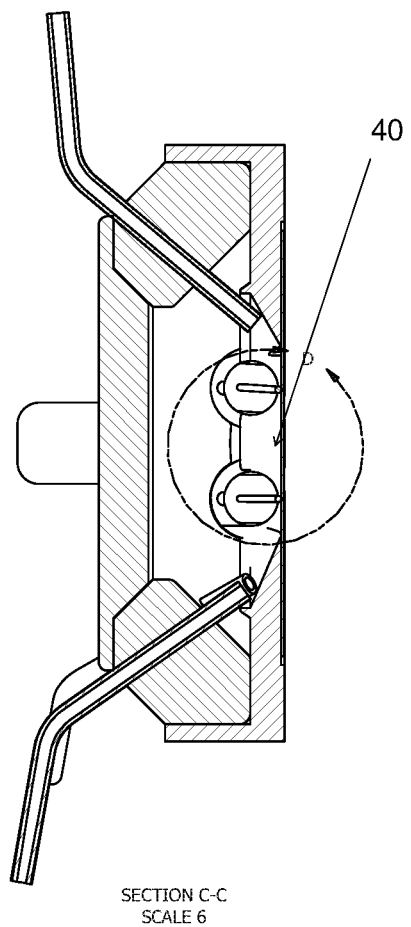
Figure 2E:
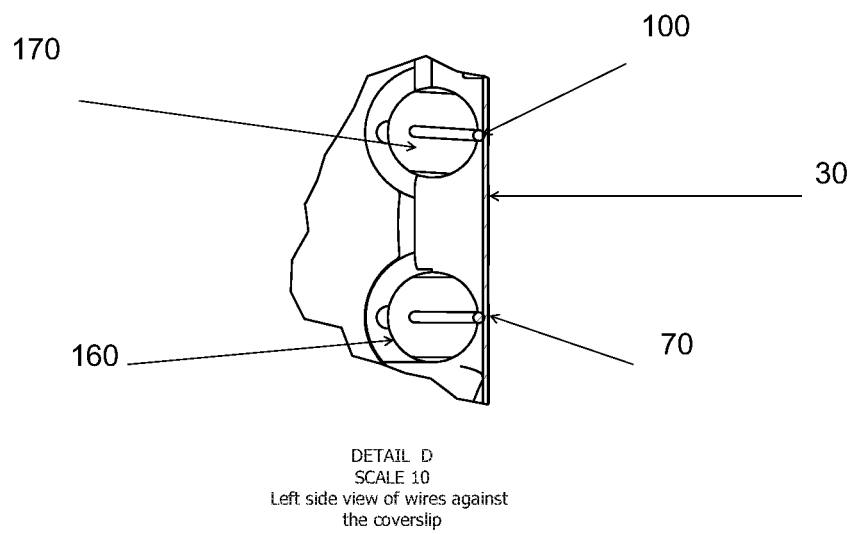

The apparatus may also include tools for micromanipulation of the cells of fibers, including impalement with micropipettes, patch clamp and other operations. In one embodiment, conical clearance at the top of the PMM is designed to allow for oblique approach of micropipettes to cells in the bay. An extra opening in the top face of the PMM (at left hand side in FIG. 4) allows for access at lower angles and remains open even when a lid, positionable over the PMM (120 in FIG. 1, and illustrated in FIGS. 2 and 3), is in place. Opening with lid in place is illustrated in FIG. 2B.

Another aspect of the present invention provides a microscope system for imaging cells. In one embodiment, the system includes an optical microscope unit and an apparatus as disclosed herein. The microscope unit will typically be one appropriate for high resolution microscopy, for example, transmitted, fluorescence, confocal, wide field, total internal reflection fluorescence or super-resolution microscopy. In such a system, the cell or fibers under observation are held against the viewing window by the cell-holding assemblies to allow for viewing of the cells by the microscope unit in "inverted microscope configuration", that is, with the microscope objective approaching from below the preparation. In certain embodiments, the cells or fibers are illuminated through the viewing window, namely, via the microscope objective. However, the present invention also encompasses further embodiments in which the cells or fibers are illuminated through a separate transparent window in the chamber housing. For example, in those embodiments including a removable lid (120), illumination of the cells or fibers may be directly from above through the top opening of the PMM (110).

The overall cross-sectional size of the apparatus can be, for example, between 2 cm and 6 cm, or 3 cm and 5 cm. In other embodiments, the size of the apparatus is chosen to be appropriate to the size of the cells or fibers under observation. A typical diameter of the chamber base assembly is 35 mm, which allows the full assembly to be placed within a heating/cooling chamber designed for use with 35 mm Petri dishes. Such is the embodiment pictured in FIG. 4.

The apparatus are described herein may be manufactured from plastic and stainless steel or similar materials. Typically, the cylinders and cell-holding wire are formed from metal. In certain embodiments, the cylinders have a diameter of between 2 and 6, or 2.5 and 5.5, or 3 and 5, or 3 and 4 millimeters in diameter. In other embodiments, the cell-holding wires have a cross section dimension of between 0.1 and 0.5, or 0.2 and 0.4, or 0.2 and 0.3 millimeters.

Preferably, the cylindrical pieces and holding wires are formed from a corrosive resistant material, for example, stainless steel. However, other materials, for example, superelastic nickel-titanium (Ni—Ti) alloys, tantalum, titanium, cobalt, chromium, nickel, molybdenum, manganese, gold, platinum, inconel, iridium, silver, tungsten, elgiloy or mixtures or alloys of any of these materials may be used. Wire material, gauge, dimensions and shape are chosen to provide adequate flexibility, in addition to force to the cell and chamber floor.

In one preferred embodiment, the chamber base assembly and the chamber PMM are formed mostly, or entirely, from 3D-printed parts. However, in other embodiments, conventional "subtractive" techniques, for example, milling, drilling and/or turning, may be combined to form part or all of these components.

In some embodiments, the chamber base and housing assemblies are formed from polymeric materials such as polyethylene terephthalate, polyurethane, polyamide, polyester (e.g. Nylon), polyorthoester, polyanhydride, polyether sulfone, polycarbonate, polypropylene, high molecular weight polyethylene, and polytetrafluoroethylene, or mixtures or co-polymers of these materials.

3D printing of the main components of the chamber allows for intricate design of the chamber base including the cell-holding bay. In particular, the shape of the cell-holding bay can be optimized to provide a flow channel with provisions for reduction of turbulence and the avoidance of overflowing, for example by the provision of retention lip. 3D printing offers many advantages in providing such features as it is an "additive" or "accretive" procedure, which, unlike conventional machining, is not limited in the shapes that can be formed. The 3-D method also allows for continuous improvement and optimization of the design of the chamber as the prototype design is stored as a digital file, which serves as the starting point for the next version. Therefore successive improvement iterations become easy to realize and test. The method also allows for inexpensive production in industrial scales. In certain preferred embodiments, the apparatus includes detachable parts allowing for the separation of the dissection/mounting from the perfusion/stimulation/imaging operations.

Yet another aspect of the present invention provides a method for viewing a cell or fiber. In one embodiment, the method includes providing an apparatus as disclosed herein and positioning the cell on the base of the cell-holding bay between the viewing window and the first and second cell-holding assemblies. The first ends of these assemblies are moved to contact differing portions of the cell or fiber so as to position and hold the cell or fiber against the viewing window. The cell or fiber may then be illuminated and viewed through the viewing window. In one embodiment, the cell is viewed through the viewing window by a microscope, for example, a confocal microscope.

In one preferred embodiment the cell or fiber is a skeletal muscle cell or fiber. However, the method is applicable to the observation of many other sample types, for example, nerve fibers and other cell types or multicellular preparations that are sized and shaped to fit between the ends of the cell-holding assemblies. Such preparations include, but are not limited to, papillary muscles, small vessels and suitable pieces of epithelia or hollow organ walls.

In various embodiments, the cell or fiber may be held to the top of the viewing window between the ends of the cell-holding assemblies. The ends of the cell-holding assemblies may be positioned to apply a stretching force to the cell at the points of contact to the cell so as to stretch the cell or fiber and achieve a firm hold that resists the flow of solution and forces introduced by pipettes and other micro-tools.

In one embodiment, the cell or fiber is held by the holding wires so as to preserve the electrical integrity and electrical functions of the cells, including electrical excitability (the ability to respond to electrical stimulation with a self-sustaining change in transmembrane electrical potential, i.e., an "action potential"). For example, the cells may be held with sufficient holding force to prevent movement of the cells away from the viewing window but with less force that is required to disrupt the electrical functions of the cells. It has been surprisingly found that the pressure applied to cut segments of muscle cells by the holding wires, while sufficient to hold the cells firmly, may be also sufficiently mild to allow the cell membrane to reseal at the pressure points, and therefore maintain the cells in a functional condition.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

We claim:

1. An apparatus for imaging cells comprising:
    a chamber base assembly comprising a viewing window;
    a cell-holding bay positioned on top of the viewing window, wherein the viewing window forms at least a portion of a base of the cell-holding bay;
    a first cell-holding assembly extending through a first conduit in the chamber base assembly and having a first end positionable at a first position in the cell-holding bay;
    a second cell-holding assembly extending through a second conduit in the chamber base assembly and having a first end positionable at a second position in the sample holding bay;
    a chamber perfusion and manipulation manifold mounted on the chamber base assembly on top of the cell-holding bay, wherein the first ends of the first and second cell-holding assemblies are movable between a first position holding the cells against the viewing window and a second position allowing placement and removal of the cells from the cell-holding bay.

2. The apparatus of claim 1, wherein the first cell-holding assembly comprises:
    a cell-holding wire forming the first end of the first cell-holding assembly;
    a linkage member having a first end connecting to the cell-holding wire and extending through the first conduit to a second end at an exterior of the chamber base assembly: and
    a handle connecting to the second end of the linkage member.

3. The apparatus of claim 2, wherein the linkage member comprises:
    a flexible member having a first end attaching to the handle; and
    a cylindrical member positioned within the first conduit and having a first end attaching to a second end of the flexible member.

4. The apparatus of claim 3, wherein the cell-holding wire is a step shaped wire comprising a first end portion, second end portion and a central portion joining the first end portion to the second end portion.

5. The apparatus of claim 4, wherein first end portion of the cell-holding wire extends substantially perpendicularly from an eccentric hole in a second end of the cylindrical member and wherein rotation of the cylindrical member allows for positioning of the second end portion of the cell-holding wire to holding the cells against the viewing window or positioning of the second end portion of the cell-holding wire away from the viewing window.

6. The apparatus of claim 1, further comprising a fluid entry line extending from the exterior of the chamber housing, through the chamber housing to a fluid entry line end positioned to deliver fluid into the cell-holding bay, and a fluid exit line extending from a fluid exit port in the cell-holding bay, through the chamber housing to a fluid aspiration port position exterior to the chamber housing.

7. The apparatus of claim 1, further comprising a temperature control unit positioned in the chamber base and providing for temperature control of the cell-holding bay.

8. The apparatus of claim 1, further comprising a first and a second electrical connector positioned on the base of the cell-holding bay, wherein the first and second electrical connectors are in electrical contact with electrical terminals exterior to the chamber and allow for electrical stimulation of a cell positioned in the cell-holding bay.

9. The apparatus of claim 1, wherein the cell-holding bay comprises a depressed portion of the floor of the chamber base assembly and wherein a transparent window form at least a portion of the floor of the cell-holding bay.

10. The apparatus of claim 1, wherein the chamber housing comprises a removable lid.

11. The apparatus of claim 1, wherein at least a portion of at least one of the chamber base assembly and the chamber housing is made using 3D printing.

12. A microscope system for imaging cells comprising:
an optical microscope unit; and
a chamber comprising:
- a chamber base assembly comprising a viewing window;
- a cell-holding bay positioned on top of the viewing window;
- a first cell-holding assembly extending through a first conduit in the chamber base assembly and having a first end positionable at a first position in the cell-holding bay;
a second cell-holding assembly extending through a second conduit in the chamber base assembly and having a first end positionable at a second position in the sample holding bay;
a chamber housing mounted on the chamber base assembly and enclosing the cell-holding bay,
wherein the first ends of the first and second cell-holding assemblies are movable between a first position holding the cells against the viewing window and a second position allowing removal of the cells from the cell-holding bay,
wherein the chamber is positioned to allow cells held against the viewing window to be viewed through the microscope unit.

13. A method of viewing a cell, the method comprising:
providing an apparatus comprising:
- a chamber base assembly comprising a viewing window;
- a cell-holding bay positioned on top of the viewing window, wherein the viewing window form a base of the cell-holding bay;
- a first cell-holding assembly extending through a first conduit in the chamber base assembly and having a first end positionable at a first position in the cell-holding bay;
- a second cell-holding assembly extending through a second conduit in the chamber base assembly and having a first end positionable at a second position in the sample holding bay;
- a chamber housing mounted on the chamber base assembly and enclosing the cell-holding bay,
- wherein the first ends of the first and second cell-holding assemblies are movable between a first position holding the cell against the viewing window and a second position allowing removal of the cell from the cell-holding bay;
placing the first ends of the first and second cell-holding assemblies in the second position;
positioning the cell on the base of the cell-holding bay between the viewing window and the first ends of the first and second cell-holding assemblies;
moving the first ends of the first and second cell-holding assemblies to the first position to contact differing portions of the cell so as to position the cell against the viewing window; and
viewing the cell through the viewing window, wherein the viewing is viewing through a microscope.

14. The method of claim 13, wherein the cell is a muscle cell.

15. The method of claim 13, wherein moving the first ends of the first and second cell-holding assemblies to the first position results in a stretching force being applied to a region of the cell.

16. The method of claim 13, wherein the contacting is such that the electrical integrity and electrical functions of the cell, including electrical excitability, is preserved.

17. The method of claim 16, wherein the cell is a nerve cell.

* * * * *